United States Patent [19]

Swann

[11] 4,272,682

[45] Jun. 9, 1981

[54] SPECIMEN ELEVATOR FOR AN ION MILLING MACHINE

[75] Inventor: Peter R. Swann, Pittsburgh, Pa.

[73] Assignee: Gatan, Inc., Warrendale, Pa.

[21] Appl. No.: 65,579

[22] Filed: Aug. 10, 1979

[51] Int. Cl.³ .............................................. G21N 5/06
[52] U.S. Cl. .................................... 250/442; 250/451; 250/492 B
[58] Field of Search ................... 250/492 B, 442, 440, 250/441, 309, 451

[56] References Cited

U.S. PATENT DOCUMENTS

| | | | |
|---|---|---|---|
| 2,220,973 | 11/1940 | Marton | 250/441 |
| 2,602,899 | 7/1952 | Page | 250/441 |
| 4,128,765 | 12/1978 | Franks | 250/442 |

*Primary Examiner*—Harold A. Dixon
*Attorney, Agent, or Firm*—Robert D. Yeager

[57] ABSTRACT

An ion milling machine specimen elevator comprising a vertically oriented piston which supports a specimen holder at its top and is movable between a lowered operating position and a raised viewing position. When the piston is in the lowered operating position, it is slowly rotated about its vertical axis by a suitable drive. The elongated piston passes through an O-ring seal into an evacuated ion milling or work chamber. At the bottom of the work chamber is disposed a pneumatic control cylinder into which the piston extends. The piston can be moved up or down by altering the pressure in the pneumatic cylinder. During ion milling the piston is at its lowest position in the evacuated work chamber and is held there by pressurized gas in the pneumatic control cylinder. A second small chamber is provided above the work chamber for specimen viewing and specimen exchange. The disclosed specimen elevator can move the specimen into the second chamber and at the same time provide a seal so the work chamber does not lose vacuum during specimen viewing or exchange. If it is desired to remove the specimen from the work chamber without disturbing its vacuum, the pressure in the pneumatic control cylinder is released and the elongated piston is automatically forced to its highest position by the exerted atmospheric pressure. As the elongated piston rises to its upper position the top of the piston passes through a second O-ring seal, at the top of the work chamber, then into the small second chamber. As the piston moves into the small second chamber, it seals the work chamber from the small second chamber so air admitted to the second chamber does not enter the work chamber. The small chamber can be lifted from the larger work chamber after the internal pressure of the small chamber is raised to atmospheric. Removing the small chamber exposes the specimen holder, allowing the specimen to be removed or closely examined to study the progress of the ion milling operation. The specimen is reinserted into the work chamber by replacing and then evacuating the small chamber and then by repressurizing the pneumatic control cylinder. This forces the piston to move through the seal between the work chamber and the small chamber to its lowest position. The piston has a beveled gear attached thereto which engages a driven bevel gear when the piston is in the lowered operating position to slowly rotate the specimen in the work chamber.

17 Claims, 3 Drawing Figures

SPECIMEN ELEVATOR FOR AN ION MILLING MACHINE

BACKGROUND OF THE INVENTION

1. Field of the Invention

This invention relates to an ion milling machine and more particularly to an ion milling machine specimen elevator and airlock mechanism which facilitates specimen viewing and specimen exchange.

2. Description of the Prior Art

Ion milling machines are used in the preparation of electron microscope specimens. An article entitled "An Improved Ion Thinning Apparatus" by A. H. Heuer, et al. from *The Review of Scientific Instruments*, Vol. 42, No. 8, Aug. 1971, pp. 1177–1184, which is herein incorporated by reference, provides good background information on ion milling.

Ion milling machines are employed for thinning specimens to a thickness of the order of 0.5 micrometers for examination by transmission electron microscopy. Desired thinning is accomplished by placing the specimen in the path of one or more beams of energetic ions and neutral atoms which sputter atoms from the specimen surface. Although material removal is very slow during ion milling, this procedure does much less damage to the underlying specimen than other material removal methods such as cutting or grinding. Ion milling has become widely used as a method for electron microscope specimen preparation, especially for those materials that because of their chemical nature cannot be thinned by electro-polishing or chemical polishing methods.

Ion thinning is accomplished in an evacuated chamber; usually the specimen is rotated during exposure to the ion beams to improve the uniformity of thinning across the specimen surface. In order to study the progress of the ion milling operation, the specimen must be periodically examined using a lower power microscope. This inspection is difficult in prior art ion thinning machines because material sputtered from the specimen and specimen holders coats the observation windows and sources of illumination, thereby obscuring the view of the specimen. Further, because the specimen is positioned near the center of the work chamber and is surrounded by the ion guns and other related mechanisms, the specimen must be viewed at an uncomfortably long distance.

A second deficiency of presently available ion thinning units is that the entire work chamber must be raised to atmospheric pressure before specimens can be exchanged. Raising the work chamber to atmospheric pressure has at least three disadvantages: (1) the time for specimen exchange is lengthy because a large volume of air has to be evacuated before the ion guns can be turned on; (2) the ion guns are initially less stable after exposure to atmospheric pressure and must be pumped for a long period of time before they restabilize; and (3) a costly valving mechanism is needed to isolate the work chamber from the pumping system.

In presently available ion thinning units, it is awkward to load and unload specimens. This is disadvantageous because electron microscope specimens are extremely fragile and are easily damaged by the small mechanical shocks they receive during the loading and unloading operation.

SUMMARY OF THE INVENTION

The present invention provides a specimen elevator and airlock apparatus which is quick, gentle and convenient in operation and solves many of the problems associated with prior art ion milling apparatus. The specimen elevator for the disclosed ion milling machine comprises a vertically elongated piston which supports a specimen holder at its top. The elongated piston is movable between a raised and lowered position. When the elongated piston is in the lowered position, it is rotated about its vertical axis. The elongated piston extends through an O-ring seal into an evacuated work chamber where the ion milling is accomplished. The piston can be moved either up or down by altering the pressure in a pneumatic cylinder mounted at the bottom of the work chamber around the piston. A sealing plate is disposed around the piston and provides for sealing between the piston and inner diameter of the cylinder walls and allows the piston to be rotated around its vertical axis. A motor is mounted at the bottom of the cylinder for rotating the piston when it is in its lowered position.

During ion milling the piston is at its lowered position and is held there by pressurizing the pneumatic cylinder. With the piston in its lowered operating position, the specimen lies inside the evacuated work chamber. If it is desired to remove the specimen from the work chamber without disturbing the work chamber vacuum, the pressure in the pneumatic cylinder is released and the piston automatically moves to its raised position under the force exerted by atmospheric pressure. As the piston is forced upwardly by atmospheric pressure, it passes through a second O-ring pressure seal into a small upper chamber. As the piston moves the specimen holder into the small upper chamber, a seal is provided between the upper chamber and the work chamber. Thus any air admitted to the small upper chamber will not pass to the work chamber.

Means are provided for admitting atmospheric pressure to the small upper chamber. The small upper chamber can be lifted from the top of the large work chamber when the internal pressure in the small chamber rises to atmospheric. This exposes the specimen holder and thus permits removal of the specimen or close examination of the specimen to study the progress of the ion milling operation. The specimen is reintroduced into the work chamber by first replacing and evacuating the small chamber, and then repressurizing the bottom control cylinder. When the control cylinder is pressurized, the piston is forced to move downwardly to its lowered operating position. As the piston moves downwardly, the seal between the upper chamber and the working chamber is eliminated and the two chambers are in open communication. The small upper chamber is held to the working chamber by atmospheric pressure.

A driven bevel gear is provided at the bottom of the control cylinder. A mating bevel gear is attached to the piston. When the piston is in its lowered position, its attached bevel gear engages the driven bevel gear causing the piston to slowly rotate. The specimen holder is mounted on the top of the piston and, therefore, specimens can be held in place simply by the force of gravity. This arrangement makes unnecessary the use of mechanical clamps and the consequent risk of physical damage to the fragile specimen.

It is an object of the present invention to provide a mechanism which enables a specimen undergoing ion thinning to be raised quickly from the center of the work chamber to a more convenient viewing position and also to quickly lower the specimen back to its normal working position after inspection.

It is another object of the invention to provide an ion milling machine having a specimen elevator device which raises the specimen to a viewing or exchange position and at the same time maintaining the working chamber in a sealed condition.

It is yet a further object of this invention to provide a specimen handling apparatus for an ion milling machine which simplifies specimen handling and is quick and gentle in operation.

DESCRIPTION OF THE DRAWINGS

For a better understanding of the present invention, reference may be had to the following detailed description taken with the accompanying drawings in which.

DETAILED DESCRIPTION OF THE PREFERRED EMBODIMENT

Figure 1:
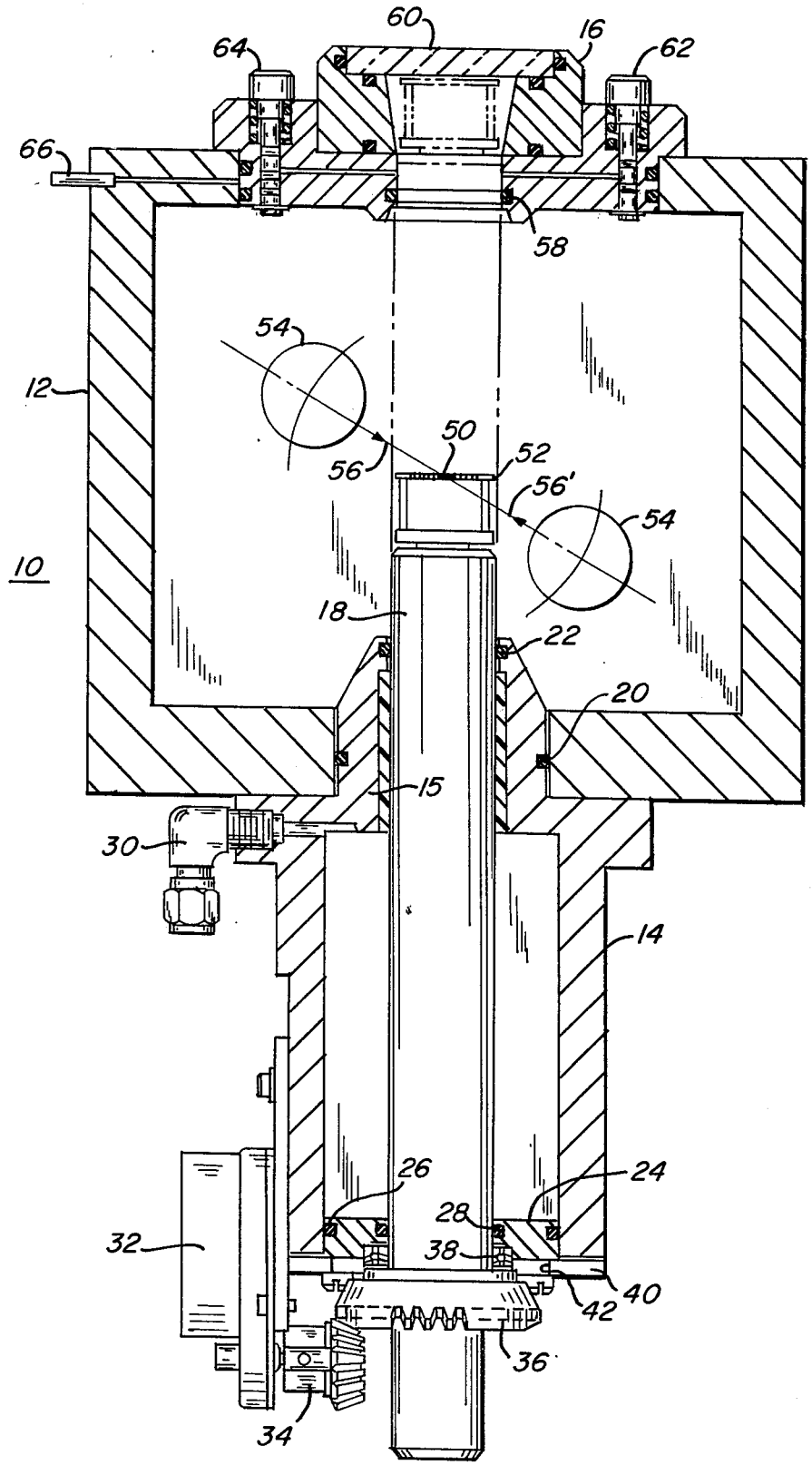
FIG. 1 is a view partially in section of a portion of an ion milling machine embodying the present invention.
Figure 3:
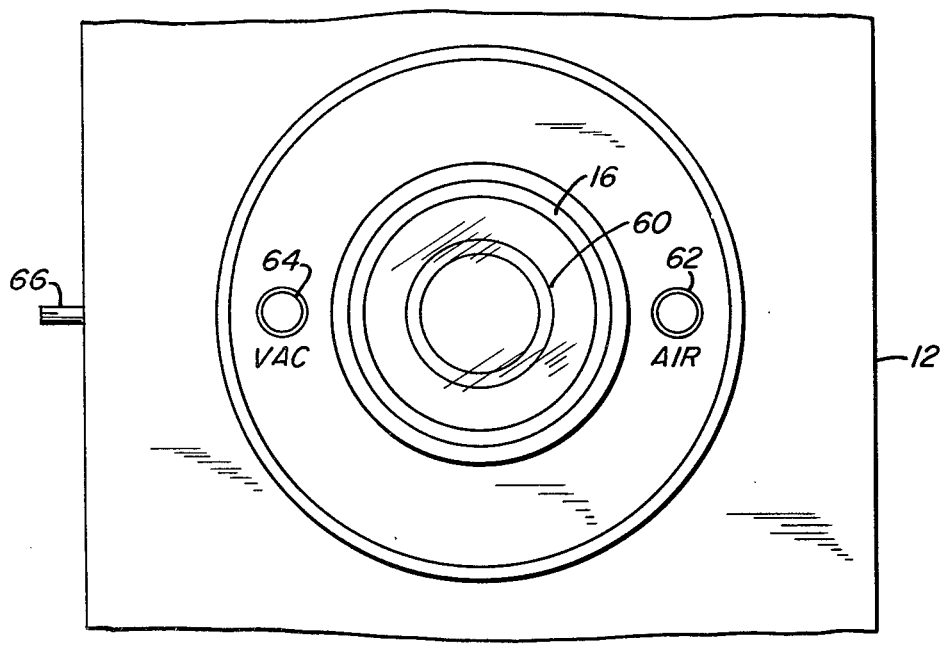
FIG. 3 is a top view of the apparatus shown in FIG. 1.
Figure 2:
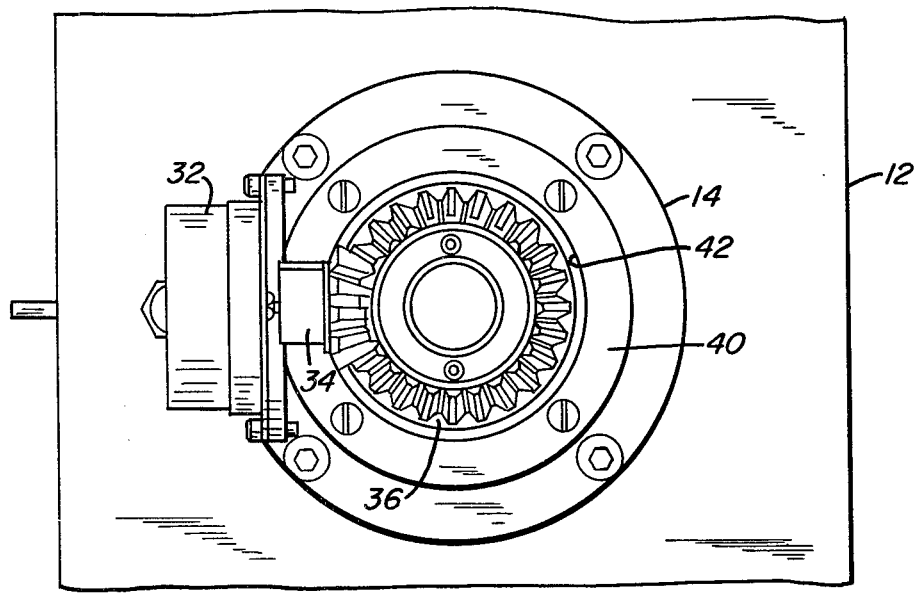
FIG. 2 is a bottom view of the apparatus shown in FIG. 1.

Referring now to the drawings, there is shown an ion milling machine, generally designated by the reference numeral 10, having a main working chamber 12, a specimen positioning cylinder 14 and a small upper chamber 16. A piston 18 is disposed for vertical movement in cylinder 14 and extends into working chamber 12. Positioning cylinder 14, having a neck portion 15, is secured to the bottom of working chamber 12. An O-ring seal 20 is provided around neck 15 which extends from cylinder 14 into the lower portion of working chamber 12. A vacuum tight seal is thus provided between neck 15 and work chamber 12.

Elongated piston 18 extends through the neck 15 of positioning cylinder 14 and into working chamber 12. An O-ring seal 22 provides a seal between piston 18 and the neck 15 of positioning cylinder 14. A sealing plate 24 is slidably disposed within cylinder 14 around piston 18. Sealing plate 24 includes an O-ring seal 26 which provides a pressure seal between sealing plate 24 and the inner wall of cylinder 14. Another O-ring seal 28 provides a seal between sealing plate 24 and piston 18. Bearing 38 is provided between sealing plate 24 and piston 18 to facilitate rotation of piston 18 during ion milling operations.

A port 30 is provided for communicating with the inside of cylinder 14. Piston 12 is held in its lowered operating position as shown in FIG. 1 by admitting pressurized gas into cylinder 14 through port 30. The pressurized gas entering cylinder 14 through port 30 forces sealing plate 24 downwardly and this in turn moves piston 18 toward its lowered position. A stop plate 40 is provided on the bottom of cylinder 14. As sealing plate 24 is forced downwardly, it engages and is stopped by stop plate 40. Atmospheric pressure tends to bias piston 18 upwardly because working chamber 12 is evacuated. However, the pressurized gas admitted through port 30 and acting upon sealing price 24 overcomes this upward bias and moves piston 18 to its lowered position.

In its lowered position, piston 18 is rotated about its vertical axis by a drive motor 32 acting through meshed nylon bevel gears 34 and 36, the latter being secured to the bottom of piston 18. Stop plate 40 has an opening 42 formed therethrough which is larger in diameter than bevel gear 36. Bevel gear 36 can thus pass through opening 42 and move into cylinder 14 when piston 18 moves upwardly.

A specimen 50 to be thinned by ion milling machine 10 is mounted on the horizontal top surface of specimen holder 52 which is screwed onto the top of piston 18. Ion guns 54 are movably mounted within work chamber 12. Ion guns 54 direct beams of ions along paths 56 and 56' to the upper and lower surfaces, respectively, of specimen 50 as it slowly rotates with the rotation of piston 18.

To raise the specimen 50 for easy viewing, the pressurized gas in positioning cylinder 14 is released and atmospheric pressure acting on piston 18 forces piston 18 to rise until it is stopped by the sealing plate 24 engaging the top of cylinder 14. A limit switch (not shown) senses the upward movement of piston 18 and stops drive motor 32; this facilitates re-engagement of bevel gears 34 and 36 when piston 18 is lowered to resume ion milling operations. A sealing O-ring 58 is disposed in the top opening of working chamber 12 to provide an air tight seal between working chamber 12 and piston 18 as piston 18 raises specimen holder 52 into smaller chamber 16. When piston 18 is in the raised position, a vacuum tight seal is thereby provided between small upper chamber 16 and working chamber 12.

A phantom view of specimen holder 52 in its fully raised position within upper chamber 16 is shown in FIG. 1. In this position, specimen 50 can be inspected at close quarters through transparent viewing window 60. If desired, small upper chamber 16 can be removed from the work chamber 12 by admitting air into the inside of the upper chamber by depressing valve 62. When the pressure inside of upper chamber 16 is raised to atmospheric, chamber 16 can be lifted away, thereby exposing specimen 50. Specimen holder 52 can then be unscrewed from the top of piston 18 to remove the specimen.

The specimen 50 on holder 52 is returned to working chamber 12 by first screwing holder 52 onto the top of piston 18. The small upper chamber 16 is then repositioned over specimen holder 52 and the air inside of upper chamber 16 is evacuated by depressing vacuum valve 64 which provides communication between upper chamber 16 and a vacuum source line 66. When chamber 16 is evacuated, pressurized gas is admitted to cylinder 14 to force sealing plate 24 downwardly and move the specimen into its normal working position in the evacuated working chamber 12. As piston 18 reaches its lowered position, the limit switch described above is actuated as bevel gears 34 and 36 engage. Motor 32 is thereby re-started to rotate piston 18 at a relatively slow speed, such as 1 rpm, to resume ion milling operations. Electrical isolation of piston 18 during ion milling operations is provided by nylon gears 34 and 36, the various rubber O-rings described above, plastic screws and washings which attach stop plate 40 to cylinder 14, and a plastic bushing within neck 15. A micro-ammeter (not shown) connected between stop plate 40 and work chamber 12 gives a continual indicaton of the ion and electron currents flowing between the ion guns 54 and the specimen 50 and specimen holder 52.

What is claimed is:

1. A machine for ion milling a specimen comprising:

a main evacuated chamber having an upper port and a lower port;

ion milling means for ion milling of a specimen disposed in said main evacuated chamber;

a secondary chamber in communication with said main chamber through its upper port for specimen viewing and exchange;

specimen positioning means extending through said lower port of said main chamber for vertically moving the specimen between a first position in said main evacuated chamber, where ion thinning is accomplished, and a second position in said secondary chamber, where the specimen can be viewed and exchanged;

means for sealing said main chamber at its lower port; and sealing means for providing a vacuum seal between said main chamber and said secondary chamber when said specimen positioning means is in the second position.

2. A machine as claimed in claim 1 wherein:

said secondary chamber is removable from said main chamber; and, said secondary chamber is held to said main chamber by atmospheric pressure when said main chamber and said secondary chamber are evacuated.

3. A machine as claimed in claim 2 wherein said secondary chamber comprises:

a transparent outer portion disposed so the specimen can be viewed when said specimen positioning means is in the second position.

4. A machine as claimed in claim 1 which further comprises:

vacuum valve means for connecting a vacuum to said secondary chamber; and atmospheric valve means for connecting said secondary chamber to atmosphere.

5. A machine as claimed in claim 1 which further comprises:

drive means for rotating said specimen positioning means when said specimen positioning means is in the first position.

6. A machine as claimed in claim 5 wherein:

said specimen positioning means comprises an elongated piston extending into said main evacuated chamber and being movable along its longitudinal axis;

said sealing means at said lower port of said main chamber includes a seal around said elongated piston where it extends into said main evacuated chamber; and, said drive means comprises:

a driven gear connected to said elongated piston for movement therewith;

a drive gear disposed to be engaged by said driven gear when said specimen positioning means is in the first position; and motor means for driving said drive gear.

7. A machine as claimed in claim 6 wherein said specimen positioning means further comprises:

a positioning cylinder disposed around a portion of said elongated piston outside of said main evacuated chamber;

a sealing plate providing a seal between said elongated piston and said positioning cylinder; and the means for admitting or exhausting pressurized gas from the positioning cylinder for causing movement of said piston along its longitudinal axis.

8. A machine as claimed in claim 7 wherein said piston is oriented vertically.

9. An ion milling machine for ion thinning a specimen comprising:

a main chamber wherein ion thinning of the specimen is accomplished under vacuum;

a specimen elevating means for moving the specimen between a lowered position where ion thinning is accomplished and a raised position where the specimen can be viewed;

said specimen elevating means comprising, an elongated piston extending into the main chamber, and a restraining cylinder disposed around a portion of said elongated piston outside of said main chamber and being constructed so that said specimen elevating means is moved to its lowered position when pressurized gas is admitted to said restraining cylinder, and said elongated piston is forced into said main chamber by atmospheric pressure when pressurized gas is released from said restraining cylinder, thereby moving said specimen elevating means to its raised position.

10. An ion milling machine as claimed in claim 9 comprising:

a secondary chamber for receiving said specimen when said specimen elevating means is in its raised position; and sealing means for sealing said secondary chamber from said main chamber when said specimen elevating means is in said raised position.

11. An ion milling machine as claimed in claim 10 comprising:

drive means for rotating said piston when said specimen elevating means is in its lowered position.

12. An ion milling machine as claimed in claim 9 wherein:

said specimen elevating means moves vertically and comprises a holder platform disposed for horizontally supporting a specimen so that the specimen can be held in place by the force of gravity.

13. An ion milling machine comprising:

a main evacuated chamber having an upper port and a lower port;

ion milling means for milling a specimen disposed in said main evacuated chamber;

a secondary chamber in communication with said main chamber through its upper port;

specimen support means extending into said main evacuated chamber through its lower port for supporting a specimen and being movable between a first position wherein said specimen is in said main chamber in position for ion milling and a second position wherein said specimen is in the secondary chamber;

means for sealing said main chamber where said specimen support means extends through said lower port of said main chamber;

sealing means for sealing said secondary chamber from said main chamber when said specimen support means moves the specimen into the secondary chamber; and drive means for rotating the specimen when said specimen support means is in the first position.

14. An ion milling machine as claimed in claim 13 comprising:

atmospheric biasing means for biasing said specimen support means to the second position by atmospheric pressure;

pressurized gas biasing means for biasing said specimen support means to the first position by utilizing pressurized gas; and release means for controllably releasing the pressurized gas from said pressurized gas biasing means to permit said specimen support means to move to the second position under the influence of atmospheric pressure.

15. In an ion milling machine having a main chamber in which ion milling of a specimen disposed therein is carried out under subatmospheric pressure, the improvement comprising:

a specimen inspection chamber in communication with said main chamber;

means for supporting said specimen within said main chamber in a first position during said ion milling and for transporting said specimen to a second position within said inspection chamber;

means for sealing said main chamber from said inspection chamber when said specimen supporting and transporting means moves said specimen into said second position;

means for biasing said specimen supporting and transporting means toward said second position by the selected application thereto of atmospheric pressure; and means for overcoming said biasing means by the selected application of superatmospheric pressure to said specimen supporting and transporting means to urge it into said first specimen position.

16. The improvement recited in claim 15 wherein:

said specimen inspection chamber is releasably connected to said main chamber, when said specimen is in said second position, by the selective application of atmospheric or subatmospheric pressure to the interior of said inspection chamber.

17. An ion milling machine for ion thinning a specimen comprising:

a main chamber wherein ion thinning is accomplished under vacuum;

a specimen elevating means for moving the specimen between a lowered position where ion thinning is accomplished and a raised position where the specimen can be exchanged;

said specimen elevating means comprising:

an elongated piston extending into the main chamber, and a restraining cylinder disposed around a portion of said elongated piston outside of said main chamber and being constructed so that said specimen elevating means is moved to its lowered position when pressurized gas is admitted to said restraining cylinder, and said elongated piston is forced into said main chamber by atmospheric pressure when pressurized gas is released from said restraining cylinder, thereby moving said specimen elevating means to its raised position;

a secondary chamber for housing said specimen when said specimen elevating means is in its raised position; and sealing means for sealing said secondary chamber from said main chamber when said specimen elevating means is in said raised position.

* * * * *

UNITED STATES PATENT AND TRADEMARK OFFICE
CERTIFICATE OF CORRECTION

PATENT NO. : 4,272,682
DATED : June 9, 1981
INVENTOR(S) : Peter R. Swann

It is certified that error appears in the above-identified patent and that said Letters Patent are hereby corrected as shown below:

Col. 3, line 64, delete "price" and substitute therefor --plate--; and

Col. 6, line 13, delete the "," and substitute therefor --;--.

Signed and Sealed this

Twenty-second Day of September 1981

[SEAL]

Attest:

GERALD J. MOSSINGHOFF

Attesting Officer

Commissioner of Patents and Trademarks